United States Patent [19]

Jackson

[11] Patent Number: 4,508,506
[45] Date of Patent: Apr. 2, 1985

[54] PROCESS AND APPARATUS FOR THE PREPARATION OF DENTAL MODELS

[76] Inventor: Robert M. Jackson, 308 S. Washington St., Clinton, Ky. 42031

[21] Appl. No.: 547,090

[22] Filed: Oct. 31, 1983

[51] Int. Cl.$^3$ .............................................. A61C 19/00
[52] U.S. Cl. ....................................... 433/74; 433/213
[58] Field of Search ............................. 433/74, 75, 213

[56] References Cited

U.S. PATENT DOCUMENTS 4,203,219  5/1980  Wiener .................................... 433/74
4,439,151  3/1984  Whelan .................................... 433/74

*Primary Examiner*—Robert Peshock
*Attorney, Agent, or Firm*—Wm. R. Price

[57] ABSTRACT

An apparatus and a method for use in dental reconstruction work in the production of cast dental models and dental dies includes a U-shaped base member having a negative cavity in its top planar surface and a complementary U-shaped member in the form of horizontally disposed plate having a series of cast dowel-like members in the form of a dental arch depending from one surface of said plate and adapted for slidable reception in the negative cavity of said U-shaped base member. The other surface of said horizontally disposed plate of said complementary U-shaped member contains a series of anchoring means which may be embedded in the unset dental stone of a positive dental model. The use of the complementary U-shaped member with its anchoring means anchored in the set dental stone of the positive dental model allows for a die to be sawed out and separated from the remainder of the model while the rest of the positive model can be permanently and positively placed in the negative cavity of said base so as to allow the die to be removed and replaced into proper position with the adjacent teeth of the model for proper use on an articulator.

9 Claims, 10 Drawing Figures

PROCESS AND APPARATUS FOR THE PREPARATION OF DENTAL MODELS

FIELD OF THE INVENTION

The invention relates to an apparatus for preparing dental prosthesis, and more particularly for a U-shaped member which contains anchoring means on one surface and dowel like cast members on the other surface can be embedded in the unset stone of a dental model. One or more dies may be sawed from the dental model with their depending dowel-like members and the positive dental model can be placed in a complementary cavity of a base member so as to allow for replacement and removal of the dies in proper relation to the adjacent teeth of the model during the restoration work.

SUMMARY OF THE PRIOR ART

To form the model of teeth which are to be prepared, it is usual practice to prepare a negative impression. After this is done a dowel pin is placed substantially in the center of the negative impression of the particular tooth that requires work. With the dowel pin in position, a first layer of die material has set up hard, a second layer is made by casting a base stone on top of the first. This base stone is usually made separable from the original impression of the teeth by a separation layer of wax or of silicon material. The cast material is sawed in the area of the tooth or teeth requiring restoration and the tooth die, or dies, are simply lifted from the mold after first cutting the first die material with the saw from the adjacent cast material. The die section is then removed by lifting the replica of the tooth. There is a problem in properly placing and allowing the die pins to set in the ngative tooth impression. Various methods previously used have been both tedious and time consuming. It has been previously recognized, for example, in U.S. Pat. No. 3,469,316, that there is a problem with properly positioning the dowel pin in the middle of the negative impression or on an inclined axis. If the longitudinal axis to the dowel pin is located at a substantial angle relative to the vertical axis of the tooth impression, the bottom may be ruined when the tooth die is separated from the base stone. On the other hand, if the dowel extends into an adjacent tooth, removal of a selected tooth die is difficult, if not impossible.

It has also been previously proposed to provide a support over the dental impression in which a great many holes are drilled. Vertically disposed rods are slidably mounted in certain of these holes and the bottom end of each is used to support one of the pins. This device, however, requires a large base, making it difficult to vibrate the impression which sometimes loosens while the stone is poured, causing the relationship of the pins to be lost. Additionally, a great amount of time is required in mounting the rods in the holes and setting the rods in the desired position. Wiener, in U.S. Pat. No. 4,203,219, disclosed a U-shaped die locator made of a disposable plastic material which was placed into the unset dental stone after having been poured into a negative dental impression to form a positive model. The Wiener die locator, however, has a second channel portion which is embedded within a suitable base material poured onto the model to form the base for the model. After the base material hardens, the model is separated from the base and the rib portion of the model are cut into model die sections which are receded on the rib portion of the base. Marshall et al provides a base portion, 11, and a liner portion, 12, with complementary grooves and ridges into which the positive model is placed and a casting composition flows into the openings around the hollow liner, 12, which is then allowed to set to a solid state to form a solid base, B, which supports the model, M, and is firmly bonded to liner, 12, and to the model, M. The liner is locked into position during the casting operation by means of locking members, 13 and 14. In any event, Marshall et al again requires two pours of the stone or investment material in order to make the positive model and the base material surrounding the positive model inside of the hollow liner, 12. Stengel, on the other hand, in U.S. Pat. No. 3,478,428, provides an arcuate base member, 11, in the form of a dental arch with a series of plastic dowel-like members, 13, projecting therefrom which is set into the unset stone of the positive dental model which is poured into the negative impression of the dental tray. Again, however, Stengel found it necessary to coat the stone with a silicon parting material, 36, and the dowel number 13 with the same material and cast a base, 39, over the projecting dowels, 13 and the retaining "nuggests," 37. In this way it was possible for Stengel to separate the positive model and the individual dowel members from the base, 39, after sawing along the lines indicated. But again, Stengel found it necessary to make two pours of stone or investment material and wait for the castings to dry for each pour before going on with his dental prosthetic work.

Camacho in U.S. Pat. No. 4,300,884, proposed a method of supporting the dowel members of a D-shaped rod, 44, which fit into certain notches of a built-up tray surrounding the conventional impression tray and thus, by use of spheres, 66, containing holes, was able to slide the dowel member, 54, along the length of the rod member and position it properly over the proper tooth requiring restorative work. Thereafter, Stengel would make his pour of stone or investment material but was silent as to how he was able to subsequently replace a die, cut from the impression, in proper juxtaposition with adjacent teeth into an articulator to see whether the articulation of the upper and lower teeth was proper to avoid locking of the cusps and valleys of upper and lower teeth during the normal process of mastication.

SUMMARY OF THE INVENTION

According to this invention, there is provided an apparatus and a process whereby a full dental arch of dowel-like members may be set into the unset stone of a positive dental model and, after hardening, locked into position in a permanent base so as to be suitable for use on a dental articulator. The U-shaped base member has a top planar surface and a negative cavity in said top planar surface which conforms generally to the shape of a dental arch. The interior walls of the negative cavity contain vertically disposed ridges and grooves. The complementary U-shaped member is set into the unset stone of the positive dental model, and consists of a horizontal plate having anchoring means on one side for anchoring with the unset dental stone. Cast dowel-like members project on the other side in the form of a simulated dental arch. The dowel-like members are formed by alternate vertical ridges and grooves which are complementary with the ridges and grooves in the interior walls of the negative cavity of the U-shaped base so that the dowel-shaped members matingly engage the ridges and grooves of the negative cavity. Additionally, indicia are added to the walls of both the horizontally disposed plate of the U-shaped member and the wall of the U-shaped base so that, when a die is cut from the positive model, including the dowel-like members depending therefrom, it is possible to match up the die through the indicia of the base in a manner that the die is in proper juxtaposition with the adjacent teeth. In this manner, the die can be removed and reworked by the dentist and replaced into the permanent base. The entire base can be placed on an articulator and matched with the matching dental models so as to insure proper articulation between upper and lower prostheses. The significant advantage of this invention, however, is that all of this can be accomplished with only one pour of the dental stone into the negative impression so that a great saving of time and material is effected.

DESCRIPTION OF THE PREFERRED EMBODIMENT

Before describing the apparatus, some background information should be provided to assist in a complete understanding of the invention. Dowel pins are routinely used in the dental office or in dental laboratories to accurately maintain the position of a prepared tooth with adjacent dentition to provide for removing a die section during the construction of the prosthesis. The dowel pin position accurately positions the dowel pin in the center of the negative impression of the tooth, i.e., in axial allignment therewith so that the prepared crown abutment impression (after saw cuts are made) makes die removal possible after the cast is completed. Proper alignment of the pin is necessary, since placement of the pin other than at the center of the tooth impression, i.e., in the interproximal area, makes removal of the die difficult or impossible. Removal of the die from the master cast, or positive model, makes possible margin determination, i.e., ditching and finer waxing of the restoration. The ability to place the die section back into the positive model in its relationship is critical for the proper fit of the finished prosthesis. This is because it is necessary, in most instances, to place the positive model with the prosthesis on an articulator to insure that both upper and lower dental models articulate properly during the mastication process. If the cusps of the prosthesis are improper, an improper fit develops so that certain masticatory movements are impossible or uncomfortable.

Figure 1:
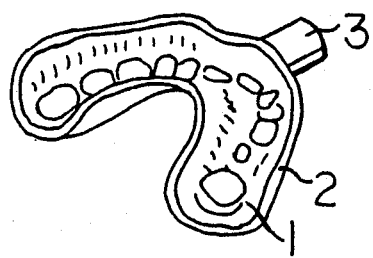
FIG. 1 is a perspective view of a full arch negative dental impression in a conventional impression tray.
Figure 2:
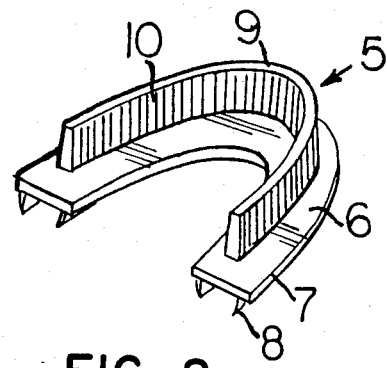
FIG. 2 is a perspective of the U-shaped member of this invention in inverted position with the cast dowel-like members projecting upwardly and the anchoring members depending from the horizontally disposed plate.
Figure 4:
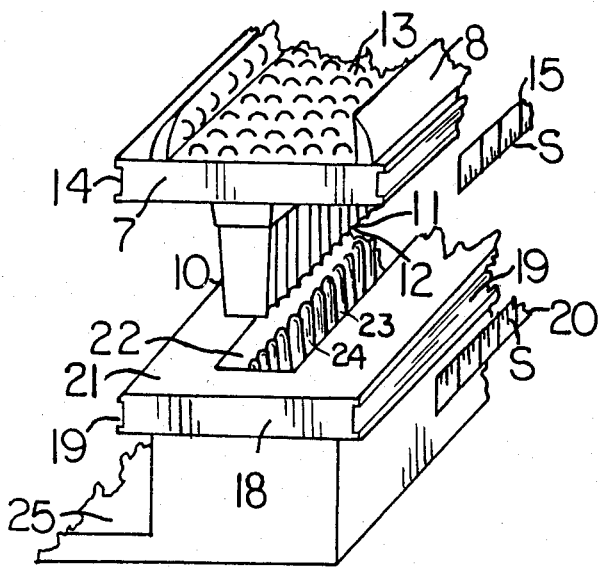
FIG. 4 is a fragmentary perspective illustrating the complementary ridges and grooves of the U-shaped base of the invention and the method of engagement of the ridges and grooves of the U-shaped member with said complementary ridges and grooves of the negative cavity of the base member.
Figure 3:
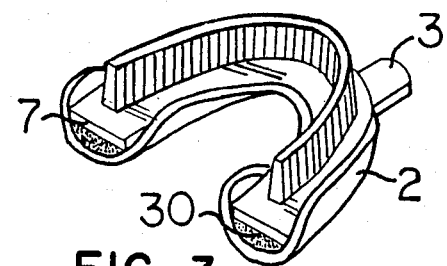
FIG. 3 is a perspective view of the U-shaped member of this invention in inverted position with the anchoring members of said member embedded in the unset dental stone poured in the dental negative impression, and with the dowel-like members projecting upwardly.
Figure 5:
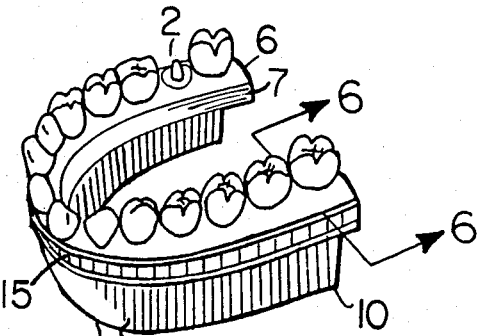
FIG. 5 is an exploded view, illustrating the positive dental model and the U-shaped member with the dowel-like members depending therefrom in position for being placed into the negative cavity of the base U-shaped member of this invention.
Figure 6:
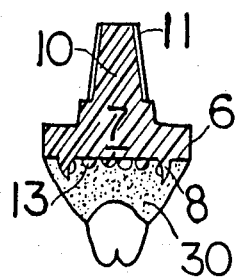
FIG. 6 is an inverted sectional view taken along line 6—6 of FIG. 5 illustrating the relationship of the case portion of the dental tooth anchored to the U-shaped member and the dowel-like member projecting upwardly from the horizontally projecting plate.

Referring now to the drawings in detail, a negative impression, 1, fabricated of conventional impression material such as hydroalkaloid, rubber based polyether, or zinc-eugenol is shown in a conventional impression tray, 2, having a handle, 3. As is well known in the art, the negative impressions have been taken directly from the patient's mouth and, when the impressions are filled with dental stone, a positive dental model will be produced. According to this invention, a U-shaped member, 5, having a horizontally disposed plate, 6, having a wall, 7, and anchoring means including inwardly turned walls, 8, on one side and raised projections, 13, on the sides of the inwardly turned walls and on the lower surface of the horizontally disposed plate, 6, are designed so as to be embedded or set into the unset stone, 30, as is illustrated in FIG. 3. A simulated dental arch, 9, made up of dowel-like materials, 10, consisting of ridges, 11, and grooves, 12, project from the other surface of the horizontally disposed plate. As can be seen in more detail in FIG. 4, the anchoring means consisting of the raised projections, 13, and the inwardly turned flanges or walls, 8, on the upper surface of the horizontally disposed partition, 6, are admirably suited for setting in the dental stone, 30. Depending from the lower surface of the horizontally disposed surface, are the dowel-like members, 10, which consist of ridges, 11 and grooves, 12. These ridges and grooves are designed so as to matingly engage with the ridges, 24, and grooves, 23, of the negative cavity, 22, of the U-shaped base member, 16. The wall, 7, of the horizontally disposed plate of the U-shaped member in one embodiment, as is clearly shown in FIG. 4, contains a groove, 14, in which a strip of indicia is fit. The indicia preferably contains scribe marks, S, on its lower surface and these match with scribe marks, S, on the indicia, 20, which fits in the groove, 19, found on the shoulder, 18, of the wall, 17, of the U-shaped base member, 16. Thus, when the dental stone, 30, has set, the positive dental model is separated from the negative impression, 1, and the impression tray, 2, and the finished unit appears somewhat as is shown in FIG. 5. It will be noted in FIG. 5, that the upper portion, is a positive model of a set of teeth with one tooth ground down in the form of a nub. The walls, 7, of the horizontally disposed plate, 6, contains groove 14 containing indicia, 15, which matches with the indicia, 20, set in the groove, 19, of the shoulder, 18 of the exterior wall, 17, of the U-shaped base member, 16. Again, the negative cavity, 22, opening into the top planar surface, 21, contains a series of grooves, 23, and ridges, 24, which mate with the grooves and ridges of the dowel grooves and ridges, 12 and 11, of the dowel-like members, 10, forming the simulated dental arch, 9, of the U-shaped member, 5. FIG. 6 illustrates the anchoring means set in the stone, 30, and illustrates further the dowel-like member, 10, and the ridge, 11.

When the dental model with the depending dowel-like members are slipped into sliding engagement with the grooves, 22, and ridges, 24, found in the negative cavity, 22, of the base model, 16, it is seen that the indicia strip, 20, located in the groove, 19, of shoulder, 18, of the U-shaped base member is in perfect registry with the indicia, 15, found in the groove, 14, of wall, 7, of the horizontally disposed plate, 6. The sectional view, taken along lines 9—9 illustrate again the mating engagement of the dowel-like member, 10, with the interior wall of the negative cavity, 22, forming the U-shaped base member, 16. Again, the relationship of the shoulder 18 of the U-shaped base member and the wall 7 of the horizontally disposed plate is shown so that the relationship of the indicia located on these members can be appreciated.

Figure 8:
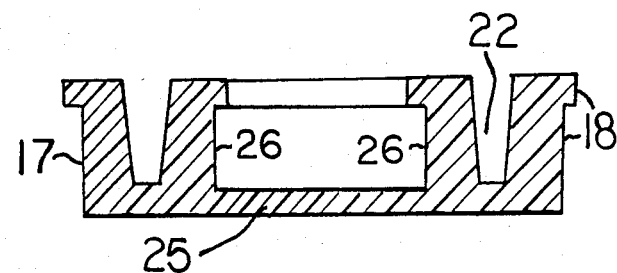
FIG. 8 is a sectional view of the U-shaped member taken along lines 8—8 of FIG. 5.
Figure 9:
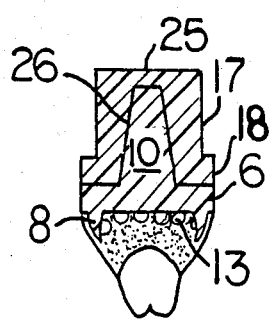
FIG. 9 is an inverted sectional view taken along lines 9—9 of FIG. 7 of a positive dental model illustrating the U-shaped member with its anchoring members embedded in the cast dental stone and the dowel-like member in mating engagement with the negative cavity of said U-shaped base member.

FIG. 8 illustrates a sectional view taken along lines 8—8 of FIG. 16. The shape of the negative cavity, 22, with sloping walls formed by the grooves, 23 and the vertical ridges, 24, and the interior walls, 26.

Figure 7:
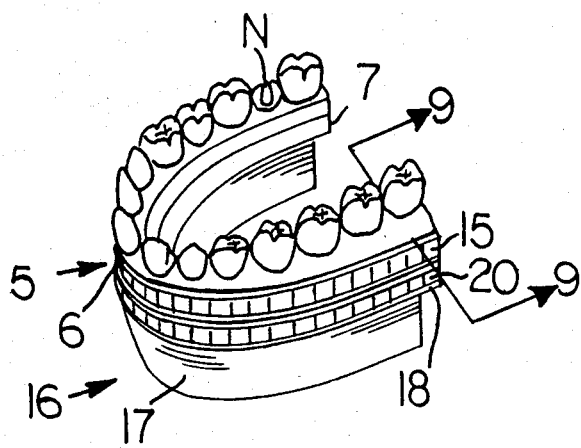
FIG. 7 illustrates the entire assembly of the cast dental model and the U-shaped member in slip-fit engagement with the base member of the invention, and illustrating the matching indicia of the horizontal plate and the matching indicia of the exterior wall of the base member when the two members are in mating engagement.
Figure 10:
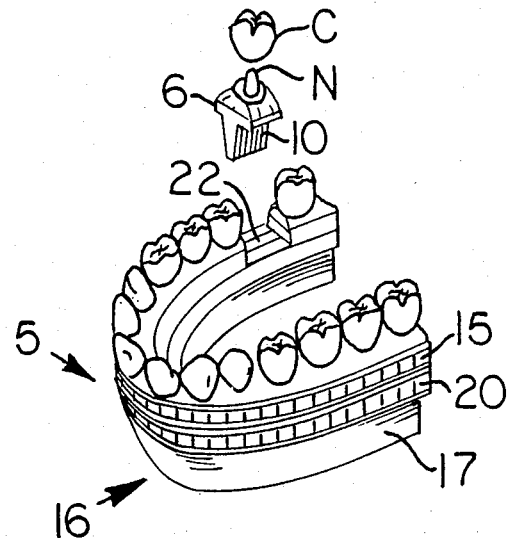
FIG. 10 is a perspective view of the dental model and the U-shaped member in mating engagement with said said U-shaped member, illustrating a die which has been sawn through the dental model and the U-shaped base member and through the dowel-like members and further illustrating a finished crown adapted for placement on the nub of the die of the dental stone model.

It is possible to mark the tooth which is to be worked upon with marks while the U-shaped member, 5, and the base member, 16 are in engagement as shown in FIG. 7. Alternately, it is possible to mark the model with the depending dowel-like members outside of the U-shaped base member, 16, and saw along the lines of the marks so as to form a die as is shown lifted free in FIG. 10. In either event, the positive dental mold is placed back into the negative cavity, 22, of the U-shaped base member, 16, while the dentist performs the fine work in ditching and fine waxing required for the preparation of the crown, C, to be placed on the nub, N. of the tooth. Thereafter, the die can be placed back into the negative cavity, 22, and the indicia, along with the scribe marks, can be used to positively line up the die with the mold. This is particularly important if several teeth are being worked on. It, thus, then becomes important to locate the exact position of a particular die relative to the remaining teeth in the model.

In any event, once the teeth have been completely finished to the dentist's satisfaction, the entire assembly, including the U-shaped base member, 16, and the U-shaped member containing the positive model with the indicia, 15 and 20, in perfect registry with each other, can be mounted onto an articulator so that the dentist can then determine whether or not the lower set of teeth are in proper relation to the upper set of teeth so as to allow the various masticulatory motions required for the chewing of food.

It should be apparent that I have provided herein a method whereby a positive model containing a dental arch of dowel-like members can be produced and anchored into proper position with only one pour of dental stone. Thus, it is possible to make an accurate dental prosthesis involving one or more teeth or even a complete set of teeth quickly, precisely, and which are in perfect articulation with the patient's remaining teeth.

Many modifications will occur to those skilled in the art from the detailed description herein above given and such is meant to be exemplary in nature, except so as to be commensurate in scope with the appended claims.

I claim:

1. A two-piece device for use in dental reconstruction work in the production of cast dental models from dental stone which comprises:
   A. a reusable U-shaped base member including:
      1. exterior walls containing accurately-spaced indicia;
      2. a top planar surface;
      3. a negative cavity in said top planar surface, conforming generally to the shape of a dental arch and having interior walls containing vertically-disposed ridges and grooves;
   B. a complementary disposable U-shaped member in the form of a horizontally-disposed plate having exterior side walls and including:
      1. a series of cast solid dowel-like members in the form of a simulated dental arch depending from one surface of said plate;
         a. said dowel-like members being formed by alternate vertical ridges and grooves,
         b. said vertical ridges and grooves of said dowel-like members slidably mating with the vertically-disposed ridges and grooves of the negative cavity of said reusable U-shaped base member, and
         c. said horizontally-disposed surface of said plate snugly fitting against the planar surface of said base member;
      2. anchoring means on the other surface of said horizontally-disposed plate for positively bonding of said plate with the unset stone of said cast dental model; and
      3. accurately-spaced indicia on said side walls, which match the indicia of the side walls of said base member.

2. A device, as defined in claim 1, in which:
   A. the interior walls of said negative cavity of said base member taper inwardly, and
   B. the cast solid dowel-like members taper inwardly from top to bottom at the same angle as the taper of the walls of said negative cavity.

3. A device, as defined in claim 1, in which the vertical grooves on either side of the dowel-like member do not completely meet.

4. A device, as defined in claim 1, in which said spaced indicia involve color.

5. A device, as defined in claim 1, in which said indicia involve scribe marks.

6. A device, as defined in claim 1, in which said anchoring means include inwardly turned walls.

7. A device, as defined in claim 1, in which said anchoring means include a series of raised projections.

8. A method of making a positive dental model with removable die sections from a dental impression which comprises the steps of:
   A. pouring dental stone into said dental impression,
   B. placing a disposable U-shaped plate member having exterior side walls marked with accurately-spaced indicia, anchoring means on one planar surface and a series of depending solid dowel-like members cast in the form of vertical ridges and grooves in the general shape of a simulated dental arch on the other planar surface, anchoring means down into the unset stone;
   C. allowing said dental stone to set;
   D. separating the dental positive model and said U-shaped plate member embedded therein from said negative impression;
   E. providing a reusable U-shaped base member having a negative cavity of complementary shape to said simulated dental arch of said dowel-like members, having interior walls which contain complementary ridges and grooves for engagement with the ridges and grooves of said dowel-like members and exterior walls with accurately-spaced indicia marked thereon, which match the indicia of the walls of said disposable U-shaped plate member;
   F. marking lines along the positive model for the required die or dies requiring restoration work;
   G. sawing the positive model along the mark lines to separate the die from the positive model;
   H. matching the indicia of the walls of said disposable plate with the indicia of the walls of said reusable base member;
   I. sliding the positive model, absent the sawed-out dies, into the negative cavity of said base member and engaging the ridges and grooves of said simulated dental arch of said dowel-like members with the complementary ridges and grooves of said negative cavity of said base member;
   J. performing the required work on the removed dies;
   K. matching the indicia on the wall of the die with the indicia of the reusable base member; and
   L. replacing the reworked die in the base in proper juxtaposition to the original teeth of the positive model.

9. A method of making a positive dental model, as defined in claim 8, the improvement of:
   A. sliding said simulated dental arch of dowel-like members into said negative cavity of said base member and engaging the ridges and grooves of said simulated dental arch of said dowel-like members with the complementary ridges and grooves of said negative cavity of said base member; and
   B. removing the positive model, including the depending dowel-like members from the base member and sawing along the marked lines to separate the die from the positive model.

* * * * *